United States Patent [19]

Adelstein

[11] 4,194,045

[45] Mar. 18, 1980

[54] 1-(3,3-DIARYL-3-OXADIAZOLALKYL)-4-PHENYL-4-PIPERIDINOMETHANOLS AND RELATED COMPOUNDS

[75] Inventor: Gilbert W. Adelstein, Evanston, Ill.

[73] Assignee: G. D. Searle & Co., Skokie, Ill.

[21] Appl. No.: 864,989

[22] Filed: Dec. 27, 1977

[51] Int. Cl.$^2$ ............................................. C07D 413/06
[52] U.S. Cl. ................................... 546/209; 424/267; 546/194; 546/210; 546/236; 546/230
[58] Field of Search .................. 260/293.67; 546/194, 546/210, 211, 209

[56] References Cited

U.S. PATENT DOCUMENTS

| | | | |
|---|---|---|---|
| Re. 29,556 | 2/1978 | Adelstein | 260/293.67 |
| 2,604,475 | 7/1952 | Sperber | 260/293.67 |
| 3,833,580 | 9/1974 | Gotz et al. | 260/293.67 |
| 3,917,615 | 11/1975 | Adelstein | 260/293.67 |
| 3,998,832 | 12/1976 | Adelstein et al. | 260/293.54 |
| 4,003,904 | 1/1977 | Adelstein | 260/293.67 |
| 4,017,491 | 4/1977 | Adelstein | 260/293.67 |
| 4,053,477 | 10/1977 | Yen | 260/293.67 |

FOREIGN PATENT DOCUMENTS 2514229  10/1975  Fed. Rep. of Germany ...... 260/293.67

*Primary Examiner*—John D. Randolph
*Assistant Examiner*—Robert T. Bond
*Attorney, Agent, or Firm*—Joy Ann Serauskas; Michael T. Murphy

[57] ABSTRACT

This invention encompasses novel 1-(3,3-diaryl-3-oxadiazolalkyl)-4-phenyl-4-piperidinomethanols and related compounds. These compounds are useful antidiarrheal agents which possess little or no analgesic activity.

5 Claims, No Drawings

1-(3,3-DIARYL-3-OXADIAZOLALKYL)-4-PHENYL-4-PIPERIDINOMETHANOLS AND RELATED COMPOUNDS

The present invention is concerned with 1-(3,3-diaryl-3-oxadiazolalkyl)-4-phenyl-4-piperidinomethanols and related compounds. More particularly this invention is concerned with compounds of the general formula

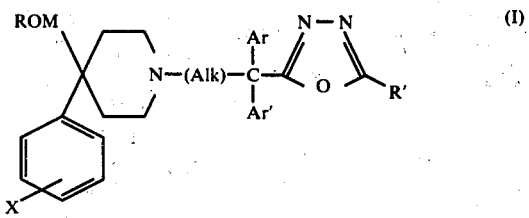

and pharmaceutically acceptable acid addition salts thereof wherein Alk is straight or branched chain alkylene containing 2-4 carbon atoms; Ar and Ar' are independently selected from the group consisting of phenyl, alkyl substituted phenyl wherein the alkyl moiety contains 1-4 carbon atoms, halo substituted phenyl or pyridyl; M is alkylene containing 1 to 4 carbon atoms; R is hydrogen, alkyl containing 1 to 4 carbon atoms or an alkanoyl containing 2-5 carbon atoms; R' is hydrogen or alkyl containing 1 to 4 carbon atoms; X is hydrogen, halogen, an alkyl radical containing 1 to 4 carbon atoms or trifluoromethyl.

The term Alk represents alkylene exemplified by ethylene, propylene or trimethylene. Ethylene is preferred.

M represents straight and branched chain aklylenes of the formula $-(C_nH_{2n})_n-$ wherein n is a positive integer from 1 to 4. Methylene and ethylene are preferred.

R and R' represent hydrogen or alkyl having 1-4 carbon atoms which are exemplified by methyl, ethyl, propyl, butyl and the branched chain isomers thereof; alkanoyl containing 2-5 carbon atoms which are exemplified by acetyl, propionyl, butyryl and isobutyryl.

X represents hydrogen halogen which is exemplified by fluoro, chloro, bromo and iodo; alkyl having 1 to 4 carbon atoms which is exemplified by methyl, ethyl, proply, butyl and branched chain isomers thereof; or trifluoromethyl.

Ar and Ar' represents phenyl; substituted phenyl radicals such as tolyl, ethylphenyl, butylphenyl, chlorophenyl, fluorophenyl and bromophenyl; and 2, 3, and 4 pyridyl.

Thus, an embodiment of the present invention is a compound of the general formula

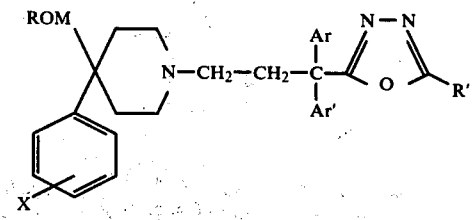

and pharmaceutically acceptable acid addition salts thereof wherein Ar and Ar' are independently selected from the group consisting of phenyl, alkyl substituted phenyl wherein the alkyl moiety contains 1-4 carbon atoms, halo substituted phenyl or pyridyl; M is alkylene containing 1 to 4 carbon atoms; R is hydrogen, alkyl containing 1 to 4 carbon atoms or an alkanoyl containing 2-5 carbon atoms; R' is hydrogen or alkyl containing 1 to 4 carbon atoms; X is hydrogen, halogen, or an alkyl radical containing 1 to 4 carbon atoms or trifluoromethyl.

Compound of the general formula

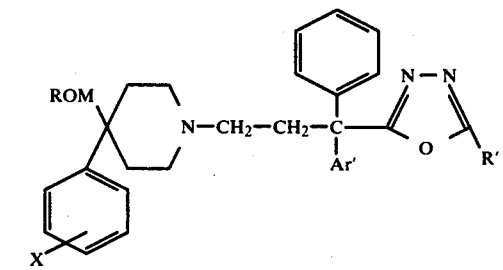

and pharmaceutically acceptable acid addition salts thereof wherein Ar' is phenyl, alkyl substituted phenyl wherein the alkyl moiety contains 1-4 carbon atoms, halo substituted phenyl or pyridyl; M is methylene or ethylene; R is hydrogen, alkyl containing 1 to 4 carbon atoms or an alkanoyl containing 2-5 carbon atoms; R; is hydrogen or an alkyl containing 1 to 4 carbon atoms; X is hydrogen, halogen, an alkyl radical containing 1 to 4 carbon atoms or trifluoromethyl.

A particularly preferred embodiment of the present invention is a compound of the general formula

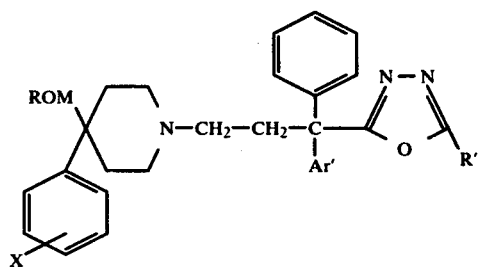

and pharmaceutically acceptable acid addition salts thereof wherein Ar' is phenyl, alkyl substituted phenyl wherein the alkyl moiety contains 1-4 carbon atoms, halo substituted phenyl or pyridyl; M is methylene or ethylene; R is hydrogen, alkyl containing 1 to 4 carbon atoms or an alkanoyl containing 2-5 carbon atoms; R' is hydrogen or methyl; and X is hydrogen, halogen, an alkyl radical containing 1 to 4 carbon atoms or trifluoromethyl.

The organic bases of this invention form non-toxic acid-addition salts with a variety of organic and inorganic acids. Such salts are formed with acids such as sulfuric, phosphoric, hydrochloric, hydrobromic, hydriodic, sulfamic, citric, lactic, maleic, malic, succinic, tartaric, cinnamic, acetic, benzoic, gluconic, ascorbic and related acids.

Compounds of the present invention are prepared by the methods set out in Scheme A

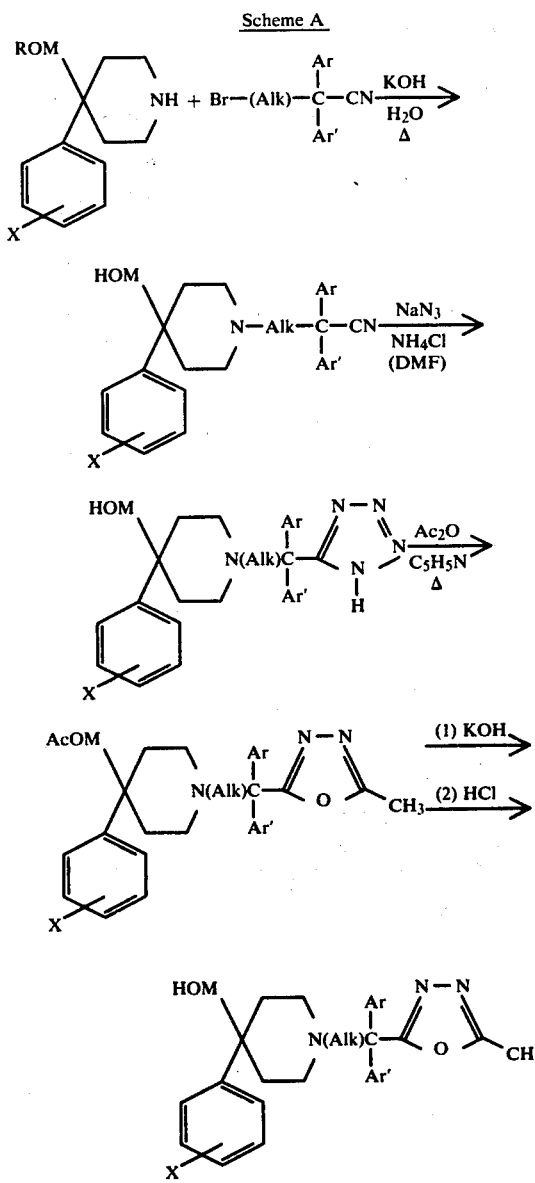

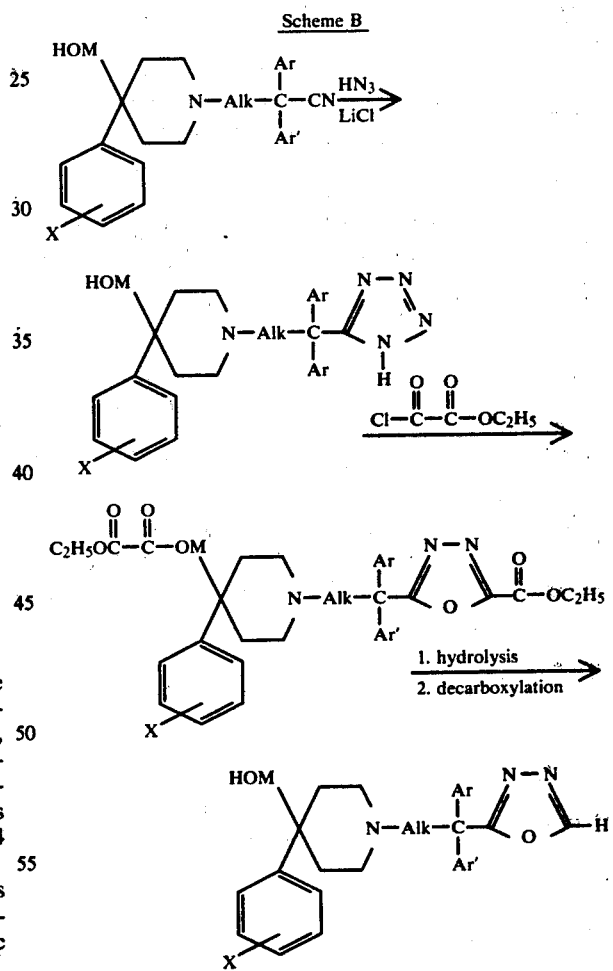

wherein Alk is straight or branched chain alkylene containing 2–4 carbon atoms; Ar and Ar' are independently selected from the group consisting of phenyl, alkyl substituted phenyl wherein the alkyl moiety contains 1–4 carbon atoms, halo substituted phenyl or pyridyl; M is alkylene containing 1–4 carbon atoms; X is hydrogen, halogen, an alkyl radical consisting of 1 to 4 carbon atoms or trifluoromethyl with the proviso that (a) when the compounds of Formula I in which R is an alkanoyl radical are desired the compounds of Formula II are esterified with a suitable anhydride in a basic medium to give the desired esters of Formula I and (b) when the compounds of Formula I in which R is an alkyl radical are desired the compounds of Formula II can be treated with sodium hydride in a suitable solvent and then further treated with an alkyl halide to give the desired ethers of Formula I.

Scheme A illustrates the preparation of compounds of the general formula I wherein R' is methyl. It would be obvious to one skilled in the art that Scheme A would also serve to illustrate the preparation of compounds of formula I in which R' could be ethyl, propyl or butyl by beginning with the appropriate starting material in order to obtain the desired compounds.

1,1-Phenyl substituted amino substituted alkyl nitriles suitable for practicing this invention are described in U.S. Pat. Nos. 3,497,519; 3,318,869; 3,299,044; 2,841,589; and 2,823,233 and an article by R. Moffett and B. Aspergran, J. Amer. Chem. Soc., 79, 4451 (1957). As shown in Scheme A, treatment of the nitrile with an azide ion by methods similar to those described by G. Moersch and D. Morrow, J. Med. Chem., 10. 149 (1967) provides the corresponding tetrazole. The tetrazole intermediates are converted to the corresponding 1,3,4-oxadiazole by treatment with an acid anhydride following the procedures substantially as described by R. Huisgen et al., Chem. Ber., 93, 2106 (1960).

Compounds of the present invention wherein R' is hydrogen and Ar, Ar', Alk, R, M, and X are defined as before are prepared by the reaction sequence set out in Scheme B.

Thus 2,2-diphenyl-4-(4-phenyl-4-piperidinomethanol) butyronitrile is reacted with sodium azide in dimethylformamide along with ammonium chloride and lithium chloride at reflux to prove 5[1,1-diphenyl-3-(4-phenyl-4-piperidinomethanol)propyl]-1H-tetrazole. This tetrazole is reacted with ethyl chloroglyoxylate in pyridine at −6° C. to provide ethyl-5[1,1-diphenyl-4-ethoxyglyoxylmethylpiperidine)propyl]-1,3,4-oxadiazole-2- carboxylate hydrochloride. This ester is hydrolyzed in aqueous potassium hydroxide to provide 5-[1,1-diphenyl-3-(4-phenyl-4-piperidine methanol) propyl]1,3,4-oxadiazole-2-carboxylic acid. Heating this acid provides 5-[1,1-diphenyl-3-(4-phenyl-4-piperidine methanol)propyl]-1,3,4-oxadiazole.

The antidiarrheal effect of the compounds of the present invention are shown by the following tests:

CECAL (Charcoal Meal Test)

Mice weighing 18–24 grams and previously fasted for 24 hours are each given orally 0.2 ml of a suspension containing 10% charcoal and 1% methylcellulose. The test compounds are administered intragastrically one hour prior to the charcoal meal. 3.5 Hours after administration of the meal the mice are sacrificed by cervical dislocation and the cecum is examined for the presence or absence of charcoal on an all or none basis. Each compound is tested at three dose levels (typically 30, 10, 3 mg/kg in groups of 6 mice per dose level. Control groups of mice given vehicle only were run concurrently with each test group.

The median effective dose ($ED_{50}$) is calculated for each compound using the logistic method of Berkson (1953).

A representative compound of the present invention 5-[1,1-diphenyl-3-(4-phenyl-4-methanolpiperidino)-propyl]-2-methyl-1,3,4-oxadiazole has an $ED_{50}$ $0.87 \pm 0.42$ in the above-identified test.

Castor Oil Induced Diarrhea in the Rat

Adult Charles River male rats were fasted in community cages for 24 hours prior to the test, with free access to water. The compound was administered intragastrically (suspended on 0.5% methyl cellulose) one hour prior to the administration of castor oil at the dose of 1.0 ml/rat intragastrically. The rats were then observed for the presence or absence of diarrhea, at hourly intervals for up to 8 hours past administration of castor oil. The median effective dose values at each hourly interval was calculated for the compound using the method of Berkson (1953).

A representative compound of the present invention 5-[1,1-diphenyl-3-(4-phenyl-4-methanolpiperidino)-propyl]-2-methyl-1,3,4-oxadiazole has an $ED_{50}$ $0.19 \pm 0.05$ at the second hour in the above-identified test.

The assessment of the analgesic effect of the instant compounds was conducted in the mouse hot plate and tail clip tests.

Mouse Hot Plate Test

A mouse (adult male weighing 18–25 grams) is placed in a restraining cylinder on a hot plate with the temperature controlled at $55° \pm 0.3°$ C. The reaction time of the mouse to lick a foot or jump is measured at 60, 40 and 20 minutes before and 30, 60, 90 and 120 minutes after administration of the test compound. The "normal" reaction time is measured as the median of the three pretreatment reaction times. A positive response consists of a reaction time greater than twice the normal time at any of the post treatment times. A dose of the test compound is considered active when 50 percent or more of the animals used show a positive response.

Tail Clip Test

A special clip is applied to the base of the tail of the mouse (adult male weighing 18–25 grams) and the time for the animal to turn around to bite at it is measured. The sensitivity of each mouse is determined one-half hour prior to drug administration. Only those mice attempting to bite the clip are included in the experiment. The test compound is then administered intraperitoneally and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response.

When tested in the above procedures 5-[1,1-diphenyl-3-(4-phenyl-4-methanolpiperidino)propyl]-2-methyl-1,3,4-oxadiazole showed very little analgesic effect.

The compounds herein described can be combined with pharmaceutically acceptable carriers to provide novel pharmaceutical compositions. The concentration of active ingredient in the composition is not critical, but is preferably 1–80%. These compositions can be administered orally, suitable forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil; olive oil, corn oil, oil of theobroma; water; agar; alginic acid; and benzyl alcohol, as well as other nontoxic compatible substances used in pharmaceutical formulations.

The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particular active ingredient can be determined by comparing its potency to that of a known standard, for which the therapeutic dosage is known. Typically 0.1–25 mg/kg is an effective antidiarrheal amount of a given compound.

Those skilled in the art will recognize that observations of activity in standardized tests for particular biological effects are fundamental to the development of valuable new drugs, both veterinary and human.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade (°C.).

EXAMPLE 1

To a solution of 52.5 parts by weight of norpethidine in 400 parts by volume of tetrahydrofuran is added 68.7 parts by weight of Red-Al(sodium bis(2-methoxyethoxy)aluminum hydride. The resulting mixture is refluxed for 0.25 hour and then stirred overnight. To the reaction mixture is added cautiously and sequentially, 13.5 parts by volume of water, 25 parts by volume of tetrahydrofuran, 10.17 parts by volume of a 20% sodium hydroxide solution, and 47.46 parts by volume of water. This mixture is then stirred for 3.0 hours. The organic phase is separated and stripped in vacuo to afford a crude solid product. This product is dissolved in methylene chloride. The methylene chloride solution is then washed with water and dried over sodium sulfate. Evaporation of the methylene chloride affords a tan solid. Crystallization of the tan solid from acetone affords 4-phenyl-4-methanol piperidine melting at 158°–160° C. This compound is represented by the following structural formula

EXAMPLE 2

5.8 Parts by weight of 4-phenyl-4-methanol piperidine, 9.9 parts by weight of 2,2-diphenyl-bromobutyronitrile, 2.0 parts by weight of potassium hydroxide pellets and 100 parts by volume of water are combined and refluxed for 5 hours. Decantation of the aqueous phase of the resultant reaction mixture affords an oil. This oil is taken up in benzene. The benzene solution is then shaken with 10% aqueous hydrochloric acid. The aqueous phase is drawn-off; the organic phase is washed with water and evaporated to afford a gummy solid. This solid is taken-up in methylene chloride. The resultant solution is slurried with aqueous potassium carbonate. The aqueous phase is drawn-off; the methylene chloride phase is dried over a drying agent and then evaporated to afford as an oil crude 2,2-diphenyl-4-(4-phenyl-4-piperidinomethanol)-butyronitrile. The crude product is chromatographed on silicic acid to give a product which is represented by the following structural formula

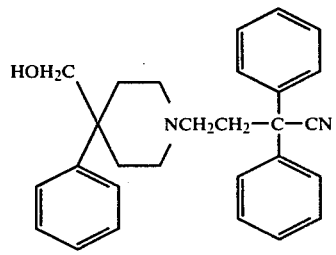

EXAMPLE 3

6.5 Parts by volume of 2,2-diphenyl-4-(4-phenyl-4-piperidinomethanol, 3.2 parts by volume of sodium azide, 2.6 parts by volume of ammonium chloride, 0.1 part by volume lithium chloride and 15 parts by volume of dimethylformamide are combined and heated at 125° C. overnight. The reaction mixture is then poured into water; the resulting solid is filtered off. Re-precipitation of this solid from a basic solution with acetic acid gave 5-[1,1-diphenyl-3-(4-phenyl-4-piperidinomethanol)-propyl]-1H-tetrazole which is represented by the following structural formula

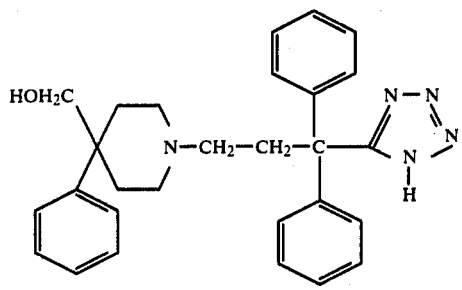

EXAMPLE 4

3.0 Parts by weight of 5-[1,1-diphenyl-3-(4-phenyl-4-piperidinomethanol)propyl]-1H-tetrazole and 10.0 parts by volume of acetic anhydride are dissolved in 20 parts by volume of pyridine and refluxed for 2 hours. The solution is cooled and the solvent is stripped off to afford a residue. The residue is slurried in water and extracted into benzene. The benzene solution is first washed with a 2% potassium carbonate solution until the washes are clear, then washed with water and then evaporated to give a brown gum. This brown gum is taken-up in benzene and then eluated on a short column of alumina to afford as an oil 5-[1,1-diphenyl-3-(4-phenyl-4-acetoxymethylpiperidinomethanol)propyl]-2-methyl-1,3,4-oxadiazole. This compound is represented by the following structural formula

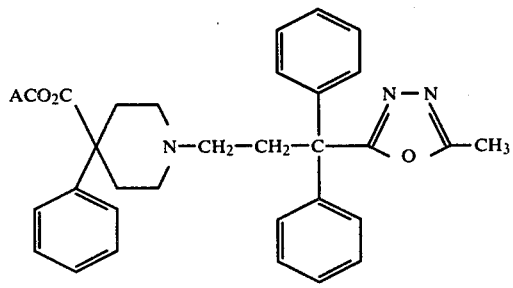

EXAMPLE 5

1.8 Parts by weight 5-[1,1-diphenyl-3-(4-phenyl-4-acetoxymethylpiperidine], 2.0 parts by weight of potassium hydroxide and 40.0 parts by volume of methanol are combined and stirred at room temperature for one hour. The solvent is evaporated and the resulting residue is slurried in water and then extracted into ethyl ether. The ethyl ether extracts are dried over a drying agent and then evaporated to afford an amorphous solid. This solid is taken up in ethyl ether. Acidification of this etheral solution with a solution of HCl/i PrOH affords a solid; the solid is collected, washed with ethyl ether and dried to afford 5-[1,1-diphenyl-3-(4-phenyl-4- methanolpiperidino)propyl]-2-methyl-1,3,4-oxadiazole, hydrochloride melting at 168°–176° C. This compound is represented by the following structural formula

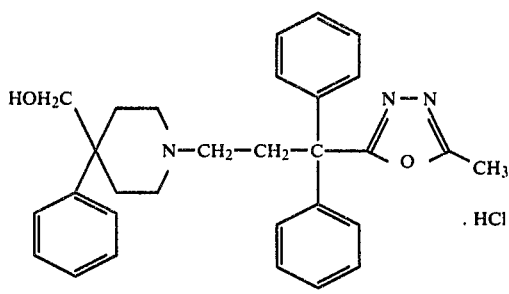

EXAMPLE 6

Substitution of an equal quantity of 1-phenyl-1-(2-pyridyl)bromobutyronitrile for the 2,2-diphenyl-bromobutylronitrile of Example 2 and substantial repetition of the procedures which are described in Examples 2, 3, 4, and 5 affords 5[1-phenyl-1-(2-pyridyl)-3-(4-phenyl-4-methanolpiperidino]propyl-2-methyl-1,3,4-oxadiazole.

EXAMPLE 7

Substitution of an equal quantity of 1-phenyl-1-(p-chlorophenyl)bromobutyronitrile for the 2,2-diphenyl-bromobutyronitrile of Example 2 and substantial repetition of the procedures which are described in Examples 2, 3, 4 and 5 affords 5[1-phenyl-1-(p-chlorophenyl)-3-(4-phenyl-4-methanolpiperidino]propyl-2-methyl-1,3,4-oxadiazole.

What I claim is:
1. A compound of the formula

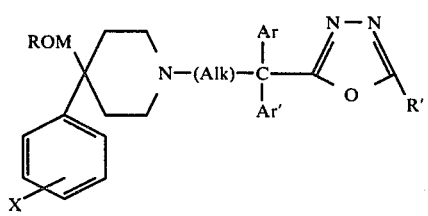

and pharmaceutically acceptable acid addition salts thereof wherein Alk is straight or branched chain alkylene having 2–4 carbon atoms; Ar and Ar' are independently selected from the group consisting of phenyl, alkyl substituted phenyl wherein the alkyl moiety has 1–4 carbon atoms, halo substituted phenyl or pyridyl; M is alkylene having 1 to 4 carbon atoms; R is hydrogen, alkyl having 1 to 4 carbon atoms or alkanoyl having 2–5 carbon atoms; R' is hydrogen or alkyl having 1 to 4 carbon atoms; X is hydrogen, halogen, alkyl having 1 to 4 carbon atoms or trifluoromethyl.

2. A compound according to claim 1 of the formula

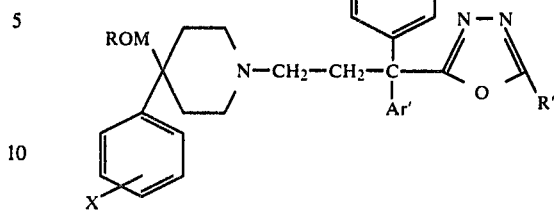

and pharmaceutically acceptable acid addition salts thereof wherein Ar' is phenyl, alkyl substituted phenyl wherein the alkyl moiety has 1–4 carbon atoms, halo substituted phenyl or pyridyl; M is methylene or ethylene; R is hydrogen or alkyl having 1 to 4 carbon atoms or alkanoyl having 2–5 carbon atoms; R' is hydrogen or methyl; and X is hydrogen, halogen or alkyl having 1 to 4 carbon atoms.

3. A compound according to claim 1 of the formula

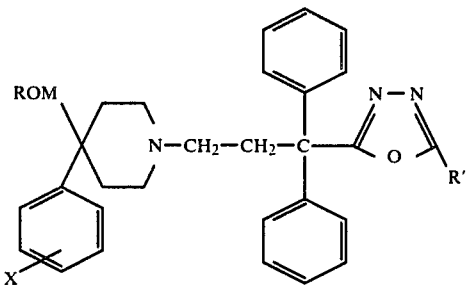

and pharmaceutically acceptable acid addition salts thereof wherein M is methylene or ethylene; R is hydrogen or alkyl having 1 to 4 carbon atoms or alkanoyl having 2–5 carbon atoms; R' is hydrogen or methyl; and X is hydrogen, halogen or alkyl having 1 to 4 carbon atoms.

4. A compound according to claim 1 of the formula

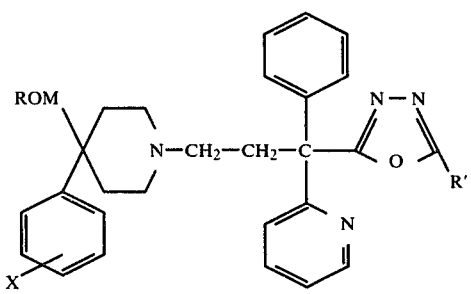

and pharmaceutically acceptable acid addition salts thereof wherein M is methylene or ethylene; R is hydrogen or alkyl having 1 to 4 carbon atoms or alkanoyl having 2–5 carbon atoms; R' is hydrogen or methyl and X is hydrogen, halogen or alkyl having 1 to 4 carbon atoms.

5. A compound according to claim 1 which is 5-[1,1-diphenyl-3-(4-phenyl-4-methanolpiperidino)propyl]-2-methyl-1,3,4-oxadiazole.

* * * * *